United States Patent
Koo

(10) Patent No.: US 6,229,612 B1
(45) Date of Patent: May 8, 2001

(54) PAPER AREA DENSITY MEASUREMENT FROM FORWARD TRANSMITTED SCATTERED LIGHT

(75) Inventor: Jackson C. Koo, San Ramon, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 09/414,176

(22) Filed: Oct. 7, 1999

Related U.S. Application Data

(60) Provisional application No. 60/103,865, filed on Oct. 12, 1998.

(51) Int. Cl.$^7$ .................................................. G01N 21/00
(52) U.S. Cl. ...................... 356/433; 250/339.1; 162/198; 162/263; 162/DIG. 6
(58) Field of Search ...................... 356/432, 433, 356/435, 436, 238.1, 238.2; 162/198, 263, DIG. 6; 250/339.1, 339.12; 378/53

(56) References Cited

U.S. PATENT DOCUMENTS

| Re. 30,884 | * | 3/1982 | Buchnea | ................................ 250/272 |
|---|---|---|---|---|
| 3,641,349 | * | 2/1972 | Dahlin . | |
| 3,904,876 | * | 9/1975 | Arendt | ................................ 250/273 |
| 4,577,104 | * | 3/1986 | Sturm | ................................ 250/339 |
| 4,840,706 | * | 6/1989 | Campbell | ............................ 162/198 |

FOREIGN PATENT DOCUMENTS

2044443 * 10/1980 (GB) .

* cited by examiner

Primary Examiner—Hoa Q. Pham
(74) Attorney, Agent, or Firm—Alan H. Thompson; L. E. Carnahan

(57) ABSTRACT

A method whereby the average paper fiber area density (weight per unit area) can be directly calculated from the intensity of transmitted, scattered light at two different wavelengths, one being a non-absorbed wavelength. Also, the method makes it possible to derive the water percentage per fiber area density from a two-wavelength measurement. In the optical measuring technique optical transmitted intensity, for example, at 2.1 microns cellulose absorption line is measured and compared with another scattered, optical transmitted intensity reference in the nearby spectrum region, such as 1.68 microns, where there is no absorption. From the ratio of these two intensities, one can calculate the scattering absorption coefficient at 2.1 microns. This absorption coefficient at this wavelength is, then, experimentally correlated to the paper fiber area density. The water percentage per fiber area density can be derived from this two-wavelength measurement approach.

6 Claims, 2 Drawing Sheets

PAPER AREA DENSITY MEASUREMENT FROM FORWARD TRANSMITTED SCATTERED LIGHT

RELATED APPLICATION

Figure 1:
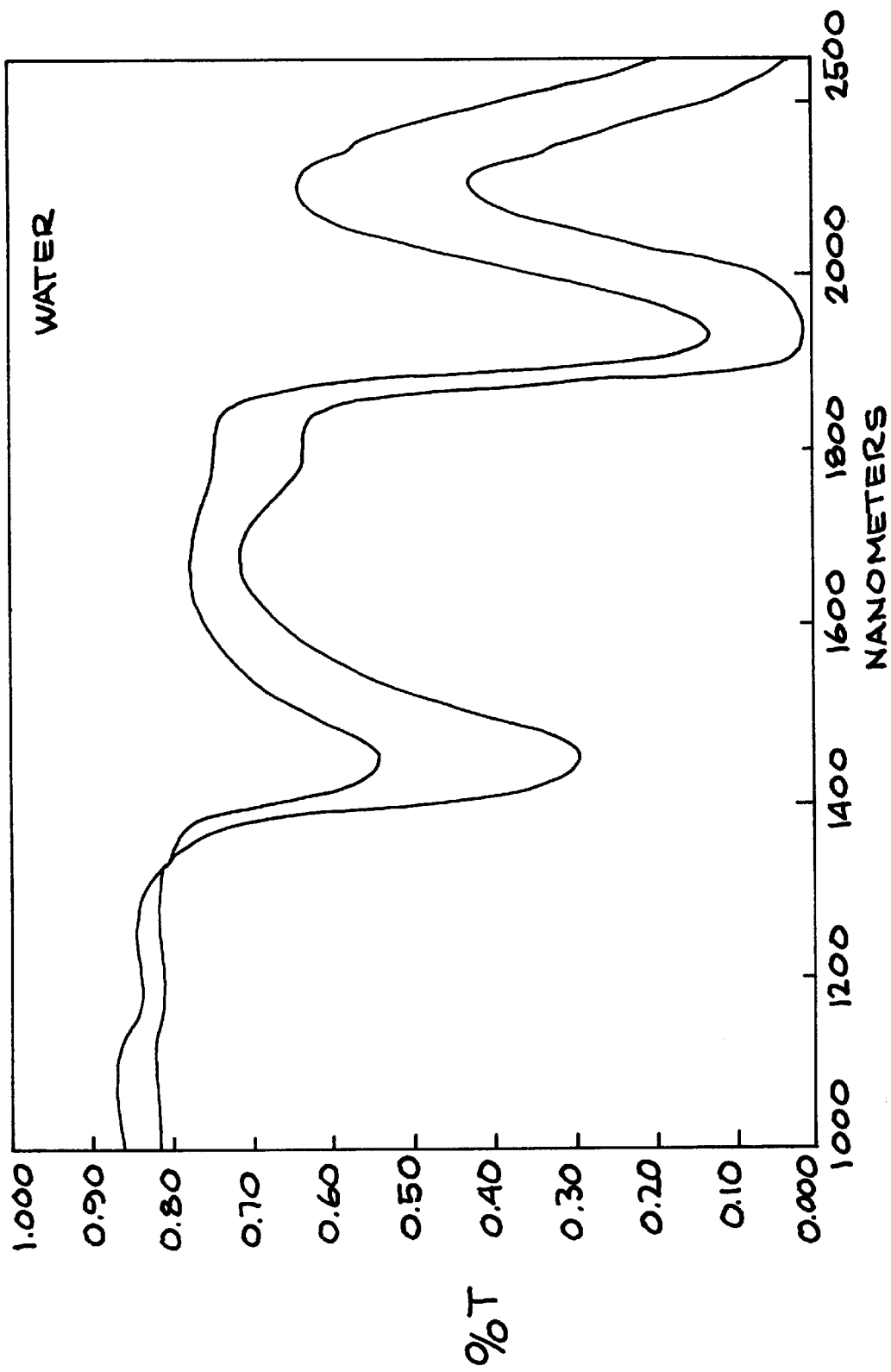

This application relates to U.S. Provisional Application No. 60/103,865 filed Oct. 12, 1998, and claims priority thereof.

The United States Government has rights in this invention pursuant to Contract No. W-7405-ENG48 between the United States Department of Energy and the University of California for the operation of Lawrence Livermore National Laboratory.

BACKGROUND OF THE INVENTION

The present invention relates to determining the average paper fiber area density, particularly to an optical method for determining the average paper fiber area density, and more particularly to an optical method for determining the average paper fiber area density (weight per unit area) from the intensity of transmitted and scattered light at a non-absorbed wavelength using a two-wavelength measurement.

The average paper fiber area density (weight per unit area) is an important parameter in the determination of paper characteristics. It is often calculated from the ratio of its dry weight and its total area. This measuring process is quite laborious and can be done only in well equipped laboratories.

Also, the measurement of the water content of paper is of great concern. Recently, an optical measuring technique for measuring water content was developed. See U.S. Pat. No. 4,840,706, issued Jun. 20, 1989 to N. F. Campbell, which was designed for point detection, wherein a modified infrared scanning gauge was used in measuring the moisture content of a paper-web during manufacturing, utilizing a measurement channel and a reference channel, with the measurement channel preferably being at a wavelength band having a center wavelength of 1.83 micron, and the reference channel preferably being at a wavelength band having a center wavelength of about 1.7 micron. The reference wavelength is remote from the measurement wavelength wherein radiation in the reference wavelength and is substantially unaffected by the moisture in the paper.

As an optical beam transmits through a sheet of paper, which is generally composed of about 20 to 30 multiple layers of cellulose fibers, more or less oriented in some preferred direction, the part of the optical beam which is not absorbed, scatters in all directions. In the forward direction, the intensity distribution of the scattered optical beam generally depends upon dielectric constant, shape, size, orientation of the paper fibers, and the scattered wavelength. In general, it is not evenly distributed. As the number of layers of cellulose fibers increases, scattering processes become more random. However, the forward transmitted optical beam becomes more uniform. Thus, in any sheet of paper, composed of 20 to 30 layers of cellulose fibers, forward scattered optical intensity may well be assumed to be uniform and isotropic. One defines this forward transmitted emission as a diffused emission and it satisfies Lambert's cosine law. See Max Born and Emil Wolf, "Principles of Optics", Fourth Edition, page 181, Chapter 4.8, Photometry and Apertures.

The present invention involves an optical measuring technique or method wherein the average paper fiber area density (weight per unit area) can be directly calculated from the intensity of transmitted, scattered light at a non-absorbed wavelength coupled with the method of using a two-wavelength measurement approach for water content measurement. Also, it has been experimentally shown that it is possible to derive the water percentage per fiber area density from the two-wavelength measurement. Thus, using this invention, paper area density measurement can be obtained from forward transmitted scattered light. In this optical measuring method, the system can be calibrated initially by an optical method: an optical transmitted intensity at 2.1 microns cellulose absorption line is measured and compared with the same scattered, optical transmitted intensity reference used for density measurement in the nearby spectrum region (1.68 microns), where there is no absorption. From the ratio of these two intensities, one can calculate the scattering absorption coefficient at 2.1 microns and calibrate the system. This absorption coefficient for this wavelength is, then, experimentally correlated to the paper fiber area density.

SUMMARY OF THE INVENTION

It is an object of the present invention to provide a method for determining the average paper fiber area density.

A further object of the invention is to provide paper area density measurement utilizing an optical measuring technique.

A further object of the invention is to provide paper area density measurement from forward transmitted scattered light.

Another object of the invention is to provide a method that will show that the average paper fiber area density (weight per unit area) can be directly calculated from the intensity of transmitted, scattered light at a non-absorbed wavelength.

Another object of the invention is to provide paper area density measurement using a two-wavelength measurement technique.

Another object of the invention is to provide an optical measuring method wherein optical transmitted intensity at one wavelength, such as 2.1 microns, cellulose absorption line is measured and compared with another scattered, optical transmitted intensity reference in the nearby spectrum region, such as 1.68 micron, where this is no absorption, and from the ratio of these two intensities, one can calculate the scattering absorption efficiency at 2.1 microns, for example, and this absorption coefficient at this wavelength is then correlated to the paper fiber area density.

Other objects and advantages of the present invention will become apparent from the following description and accompanying drawings. Basically, the invention involves paper area density measurement from transmitted scattered light based upon experimental data, using the optical measuring method of this invention. It has been shown that the average paper fiber area density (weight per unit area) can be directly calculated from the intensity of transmitted, scattered light at a non-absorbed wavelength. The experimental data has also shown that it is possible to derive the water percentage per fiber area density from a two-wavelength measurement.

In the optical measuring technique, optical transmitted intensity at 2.1 microns cellulose absorption line is measured and compared with another scattered, optical transmitted intensity reference in the nearby spectrum region (1.68 microns), where there is no absorption. From the ratio of these two intensities, one can calculate the scattering absorption coefficient at 2.1 microns. This absorption coefficient at this wavelength is, then, correlated to the paper fiber area density. This method has been experimentally verified using a 0.8–2.2 μm linear scan camera, and involved monitoring the intensity of the forward scattered optical beam through increasing layers of three different kinds of papers at 1.68 micron and at 2.1 microns wavelengths.

FIG. 1 graphically illustrates an unnormalized water absorption data at 1.94 μm with optical scattering intensities measurement at 1.94 μm NS 1.68 μm with the same light source.

Figure 2:
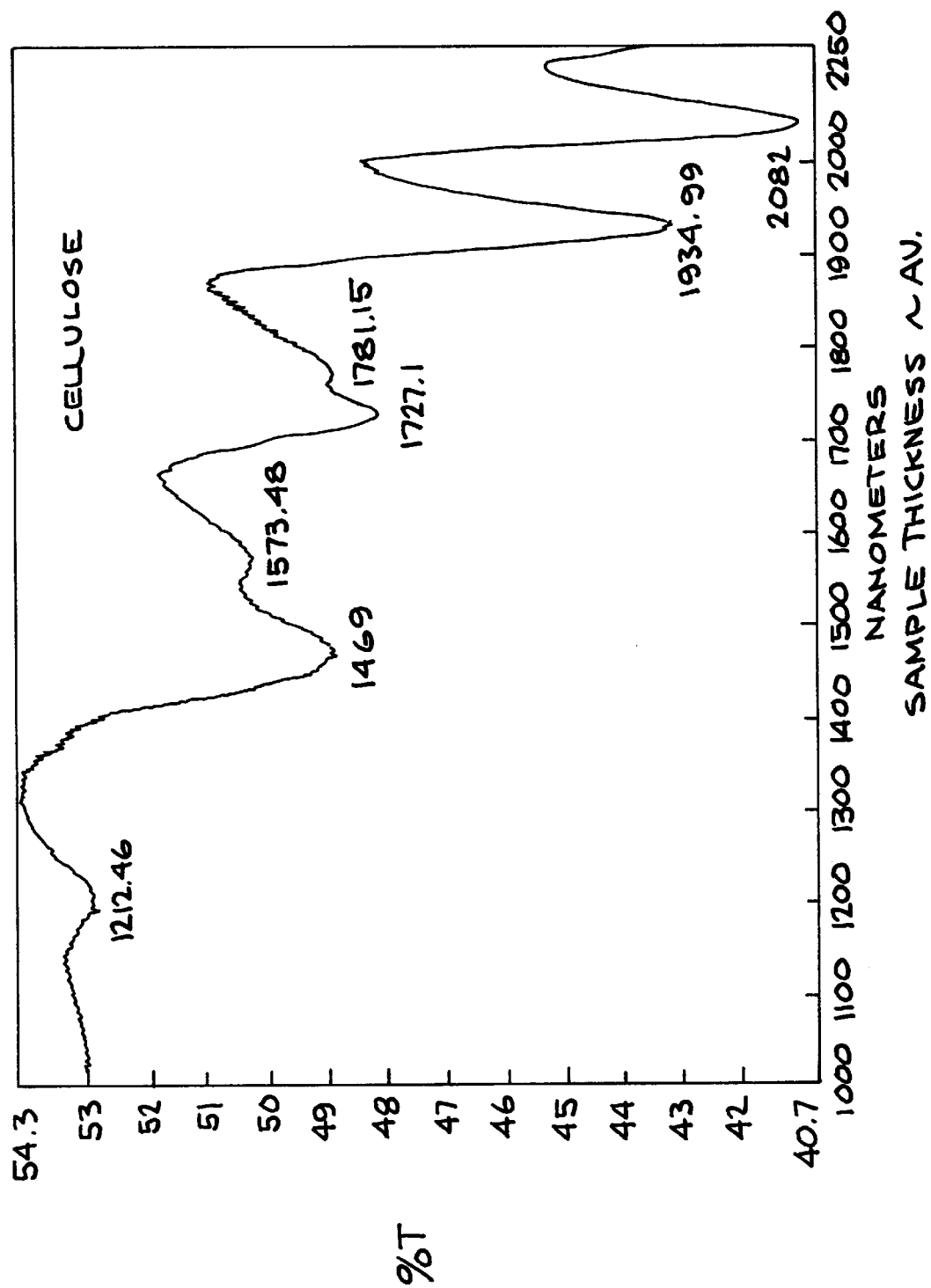

FIG. 2 graphically illustrates cellulose absorption at 2.1 micron.

DETAILED DESCRIPTION OF THE INVENTION

The present invention involves a method for determining the average paper area density and for determining the water percentage per fiber area density using a two-wavelength measurement technique. Based on experimental data, the average paper fiber area density (weight per unit area) can be directly calculated from the intensity of transmitted, scattered light at a non-absorbed wavelength. This data also shows that one can derive the water percentage per fiber area density from the two-wavelength measurement method of this invention.

In the optical measuring method of this invention, optical transmitted intensity at 2.1 microns cellulose absorption line is measured and compared with another scattered, optical transmitted intensity reference in the near-by spectrum region (1.68 micron), where there is no absorption. From the ratio of these two intensities, one can calculate the scattering absorption coefficient at 2.1 microns. This absorption coefficient at wavelength is, then, experimentally correlated to the paper fiber area density.

As pointed out above, as an optical beam transmits through a sheet of paper, which is composed of about 20–30 multiple layers of cellulose fibers, more or less orientated in some preferred direction, the part of the optical beam which is not absorbed, scatters in all directions. In this forward direction, the intensity distribution of the scattered optical beam generally depends upon the dielectric constant, shape, size, orientation of the paper fibers and wavelength. In general, it is not evenly distributed. As the number of layers increases, scattering processes become more random, and the forward transmitted optical beam becomes more uniform. Therefore, in any sheet of paper, composed of 20–30 layers of cellulose fibers, forward scattered optical intensity may well be assumed to be uniform and isotropic, this forward transmitted emission being defined as a diffused emission. It is in this sense, that one can define the scattering absorption coefficient (Alpha). It is also in the same sense, that one can define a scattering attenuation coefficient (SAC). SAC describes the loss of light intensity in the forward scattering direction as an optical beam transmits through certain thickness or layers of paper. Since the Alpha of the paper fibers depends on the validity of the SAC at a non-absorption wavelength and both of them describe the characteristics of the paper fibers, if one can assume the distributions of the dielectric constant, size and shape, orientation of the paper fibers in a particular paper is the same, then both coefficients (Alpha and SAC) are constants and should be related through the ratio of their values. Then one should be able to use the SAC to describe the area density of the paper fibers in a paper web provided it is first calibrated in the laboratory. In doing so, one saves the need of an optical detector at 2.1 microns.

The experimental verification was carried out using a 0.8–2.2 μm linear scan camera, such as the InGaAs Line Scan Camera made by Sensors Unlimited, Inc. and involved monitoring the intensity of the forward scattered optical beam through increasing layers of three different kinds of papers at 1.68 micron and 2.1 microns wavelengths. At 1.68 micron, the slope of the negative logarithmic values of the average measured optical intensities is defined as SAC per sheet (SAC/S) of the particular paper at this wavelength. By substituting the thickness of the sheet of paper, one gets the number for SAC per thickness. At 2.1 microns, the slope of the negative logarithmic values includes the scattering absorption coefficient per sheet (Alpha/S) of the paper fiber and the SAC per sheet. If the SAC/S values at the two wavelengths are the same, the scattering absorption coefficient per sheet (Alpha/S) of paper fiber can be derived from their difference. The experimental results are set forth in Table 1.

TABLE 1

| | SAC Data | | |
|---|---|---|---|
| | IBM (Xerox) | Eaton Air | Strathmore Tracing |
| Dry Area Density Mg/cm^2 | 7.44 | 3.399 | 4.492 |
| Thickness/s (mm) | 0.1 | 0.056 | 0.044 |
| SAC/s (1.68 μm) = Ln($I_s$) | 0.7195 | 0.2682 | 0.1887 |
| SAC/s (2.1 μm) = Ln($I_{s1}$) | 1.7391 | 0.7060 | 0.4881 |
| Alpha/s = Ln($I_{s1}$) − Ln($I_s$) | 1.0196 | 0.4378 | 0.2994 |

Ln($I_s$), Ln($I_{s1}$) are the logarithmic values for transmitted optical intensity at these wavelengths.

From the experimental data, one sees that the values for SAC and the Alpha at 2.1 microns are constants. One can use either SAC or Alpha values per sheet at 2.1 microns to relate with the paper fiber density per sheet. In other words once it is calibrated, one need not use the cellulose absorption line in the field.

From Table 1, it can be seen the Alpha values of these three different papers is quite linearly proportional to their thickness. It may well be that in these cases the thickness of the papers seems determined only by their fiber density. However, this is not true for the SAC/S values of different papers at 1.64 μm, especially not for the values for area density. This may well be due to different kinds of paper having different amounts of various different fillers. The SAC values at 1.68 μm include the scattering effect from the fillers, but not for the Alpha values. Different fillers are also different in weight.

In the water percentage measurement, the SAC value of a particular sheet of paper changes with a different percentage of water. However, in the two-wavelength method, one can measure the water percentage from the difference of logarithmic values of the normalized optical intensities at the two different wavelengths: one at the water absorption wavelength and one without absorption (SAC value). See above-reference U.S. Pat. No. 4,840,706 and copending application Ser. No. 09/386,533 filed Aug. 30, 1999 entitled "System and Method for 100% Moisture and Basis Weight Measurement of Moving Paper", assigned to the same assignee. If one again compares this measured SAC value with a pre-calibrated SAC value per unit fiber area density for this paper at this measured water percentage, one can directly calculate the paper fiber density per area.

Once one measures the scattered optical intensities through a sheet of paper (under the same light source as the data above. Otherwise, one needs to use the normalized values), one can calculate its Alpha value. From the Alpha value and the graph of FIG. 1, one knows the water percentage in the paper. From FIG. 1 again, one finds what the SAC value at 1.68 μm for this water percentage at 0.1 mm should be. If the measured SAC value at 1.68 μm is different from the value indicated, the ratio of the measured SAC value to the indicated SAC value of FIG. 1 describes the percentage variation of the paper area density. If the density of this particular paper as a function of water percentage is available, one can calculate the paper thickness from these data.

It has thus been shown that the present invention provides for paper area density measurement from forward transmitted scattered light. Based on experimental data the average paper fiber area density (weight per unit area) can be directly calculated from the intensity of transmitted, scattered light at a non-absorbed wavelength The wavelengths being 2.1 and 1.68 microns, for example. From this data it has also been shown that it is possible to derive the water percentage per fiber area density from a two-wavelength measurement.

While at particular parameters, etc. for carrying out the present invention have been described and/or illustrated to exemplify and teach the principles of the invention, such are not intended to be limiting. Modifications and changes may become apparent to those skilled in the art, and it is intended that the invention be limited only by the scope of the appended claims.

What is claimed is:

1. A method for optically measuring paper fiber area density, consisting of:

measuring and comparing a first optical transmitted wavelength of about 2.1 micron at a cellulose absorption line of paper fiber area with a scattered optical transmitted wavelength reference of about 1.68 microns in the nearby spectrum region where there is no absorption, from the ratios of these two wavelengths, calculating the scattering absorption coefficient of the first intensity, and correlating the absorption coefficient to the paper fiber area density.

2. The method of claim 1, additionally including deriving the water percentage per fiber area density from the two-wavelength measurement.

3. A method for paper area density measurement from forward transmitted scattered light by:

directing 2.1 micron and 1.68 micron optical wavelengths through the papers and, directly calculating the weight per unit area from the intensity of the transmitted, scattered light from the two different optical wavelengths.

4. The method of claim 3, additionally including deriving the water percentage per fiber area density from the two wavelength calculations.

5. A An optical measuring method, consisting of:

measuring an optical transmitted intensity at 2.1 microns cellulose absorption line, measuring a scattered, optical transmitted intensity reference at 1.68 microns in the nearby spectrum region where there is no absorption, comparing the two measurements, from the ratio of these two intensities, calculating the scattered absorption coefficient at 2.1 microns, and correlating the absorption coefficient to the paper fiber area density.

6. The method of claim 5, additionally including deriving the water percentage per fiber area density from the two intensity measurement.

* * * * *